United States Patent [19]

Kao

[11] Patent Number: 5,585,543
[45] Date of Patent: Dec. 17, 1996

[54] ALTERATION OF PLANT SELF-COMPATIBILITY USING GENETIC MANIPULATION OF THE S-GENES

[75] Inventor: Teh-hui Kao, State College, Pa.

[73] Assignee: The Penn State Research Foundation, University Park, Pa.

[21] Appl. No.: 193,826

[22] Filed: Feb. 9, 1994

[51] Int. Cl.⁶ .............................. A01N 5/00; C12N 15/00; C12N 15/82
[52] U.S. Cl. .................. 800/205; 800/DIG. 40; 435/172.3; 435/240.4; 435/320.1; 536/23.1; 536/23.6; 536/24.1
[58] Field of Search ................ 435/172.3, 69.1, 435/240.4, 320.1; 800/205, DIG. 40; 536/23.6, 23.1, 24.1

[56] References Cited

PUBLICATIONS

Toriyama et al (1991) Theor Appl Genet 81: 769–776.
Napoli et al (1990) The Plant Cell 2: 279–289.
Mariami et al (1992) Nature 357: 384–387.
Ai, Y. et al., Sex Plant Reprod., 1990, vol. 3, pp. 130–138.
Ioerger, T. R. et al., sex Plant Reprod. 1991, vol. 4, pp. 81–87.
Coleman, C. et al., Plant Molecul. Biol. 1992, vol. 18, pp. 725–737.
Heslop–Harrison (1975) Ann Rev. Plant Physiol 26: 403–425.
Nasrallah et al (1986) Tredsin Genet. (TIG) 2 (9): 239–244.
Matton et al (1994) Proc. Natl Acad Sci USA 91: 1992–1997.

*Primary Examiner*—David T. Fox
*Assistant Examiner*—Elizabeth F. McElwain
*Attorney, Agent, or Firm*—Thomas J. Monahan

[57] ABSTRACT

A method for altering self-compatibility/self-incompatibility in flowering plants is presented. The method comprises manipulation of the plant genome and production of the transonic plants. Abolishment of self-incompatibility was achieved by inserting into plant genome as DNA segment comprising anti-sense message of the allelic form of the S-gene responsible for self-incompatibility. This insert prove to be satisfactory to block expression of said allelic form of S-gene. Introduction of self-incompatibility was achieved by inserting into plant genome DNA construct comprising message coding for the S-protein responsible for self-incompatibility.

14 Claims, 5 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
  ( A ) LENGTH: 51 base pairs
  ( B ) TYPE: nucleic acid
  ( C ) STRANDEDNESS: single
  ( D ) TOPOLOGY: linear  ( i i ) MOLECULE TYPE: DNA (genomic)

( x i ) SEQUENCE DESCRIPTION: SEQ ID NO:1:

CAGAACATTG ATTATATTAT CTTCTTTAAA ACGCGAATAC TTGTCGCCAG T   51

( 2 ) INFORMATION FOR SEQ ID NO:2:

( i ) SEQUENCE CHARACTERISTICS:
  ( A ) LENGTH: 54 base pairs
  ( B ) TYPE: nucleic acid
  ( C ) STRANDEDNESS: single
  ( D ) TOPOLOGY: linear  ( i i ) MOLECULE TYPE: DNA (genomic)

( x i ) SEQUENCE DESCRIPTION: SEQ ID NO:2:

CAAATCATTG ACAATTCTAT CTTTTAAGCT GAACGACACA AACTTATCTC CATC   54

ALTERATION OF PLANT SELF-COMPATIBILITY USING GENETIC MANIPULATION OF THE S-GENES

GOVERNMENT SPONSORSHIP

This invention was made with Government support under Grant No. 90-37261-5560 awarded by the U.S. Department of Agriculture and Grant No. IBN-9220145 awarded by the National Science Foundation. The Government has certain rights in the invention.

BACKGROUND OF THE INVENTION

The present invention relates to the genetic manipulation of the plants. More specifically it relates to the regulation of the serf-pollination in flowering plants.

By the way of background, for over 130 years, since Darwin observed that some plants can fertilize themselves with their own pollen while others cannot, scientists have been trying to understand exactly what controls this aspect of plant mating. The present invention, which describes a method of altering the nature of this mating, provides the first direct evidence confirming a theory of genetic self-incompatibility that is the foundation of research in plant genetics.

The cornerstone of this theory is self-incompatibility, the genetic barrier to inbreeding in flowering plants. In the simplest cases it is controlled by a single locus, the S-locus, which has a large number of alleles. In gametophytic type self-incompatibility, fertilization is blocked when the S-allele expressed by the pollen matches at least one of the two alleles carded by the pistil. The present invention describing the alteration of the self-incompatibility in petunia plants can prove especially useful in many flowering plants, either to introduce or to abolish self-incompatibility.

The ability to prevent plants from fertilizing themselves could double the yield and reduce by one-third to two-thirds the labor costs involved in hybrid seed production. Virtually all commercially important vegetables and many important flowers are produced from F1 hybrid seeds, the result of crossing two purebred plant lines. In order to assure the uniformity of hybrid seeds, growers typically must remove by hand the pollen-producing organs from the seed-producing parent plants, then discard the seed produced by the pollen parents—sacrificing half the seed crop. If the plants were 100% self-incompatible, you could harvest seed from every plant while using much less costly and more efficient fertilization procedures. In addition, the ability to control the serf-compatibility could provide the key to producing hybrids in many crops where this technique previously has been either inefficient or impossible.

Growers of self-incompatible crops could benefit from the possibility of changing the nature of the plants by transforming them into self-compatible plants. Because of this self-incompatibility, commercial apple growers typically mix, in a single orchard block, three varieties that they carefully select to provide sources of compatible pollen. Cultivation of a single self-compatible variety would increase efficiency by reducing several cultural and harvesting problems.

Confirmation that the S gene encodes the key protein in self-recognition, which is the core of the present invention, is an important step for the scientists who have published analyses based on that assumption. Many generations of scientists have devoted their lives to understanding the system of self-incompatibility in plants. The Applicant has added something to this effort that others have been seeking for half a century. The invention herein described contributes to the understanding of this biological process bringing it into the era of modern molecular biology.

SUMMARY OF THE INVENTION

In accordance with the present invention, a method to alter the self-incompatibility in the flowering plants by controlling the activity of the S-locus is presented.

A protein identified in the early 1980s seemed to be the predicted S protein, but the strongest clues until now were only from indirect evidence. By harnessing standard genetic-engineering techniques, the Applicant was able to neutralize a particular allelic form of the S-gene in a group of petunia plants, reversing their inherited inability to fertilize themselves and enabling them to produce seeds. The Applicant also inserted a particular allele of an S-gene into the genome of another group of plants, giving them the ability to reject pollen with a specific genetic identity.

Experiments were performed to show that a plant's ability to produce seeds when self pollinated depends on the presence or absence of an particular S-gene. In one experiment, an S gene was disabled in a line of self-incompatible plants, then fertilization with their own pollen was attempted. The reasoning behind this approach is that if an S protein is required for self-incompatibility interactions between pistil and pollen, then inhibition of its synthesis should lead to the breakdown of self incompatibility.

Each plant has two varieties of the S gene, called S alleles, which it inherits from the parent plants. The Applicant used petunia plants that had alleles called S2 and S3. A genetic engineering technique was used to produce an "antisense" message of a segment of the S3 allele whose DNA sequence order is the reverse of that of a normal S3 allele's.

Next, the antisense S3 allele was incorporated into a bacterium that can be used to infect petunia leaves. From these leaves grew transgenic plants containing S2, S3, and antisense S3. Antisense RNA was able to block the synthesis of protein from sense RNA.

These transgenic plants were tested and found that they were not producing any S3 protein. Thereafter, attempts were made to fertilize them with S3 pollen. A normal plant with S2 and S3 alleles, when pollinated with S3 pollen, will reject the pollen because the S allele types match. The flower's pistil recognizes the pollen as 'self pollen,' fertilization fails, and the plant does not produce seeds. Obtained transgenic petunias produced the same large number of seeds as you would get from compatible pollination, showing that they had lost the ability to reject self pollen. This is the first successful attempt to use the antisense approach in any self-incompatible plant species.

In another experiment, the Applicant put an S3 gene into petunias that contained S1 and S2 alleles. A normal plant with S1 and S2 alleles will accept S3 pollen because the S3 allele carried by the pollen is different from the S1 and S2 alleles carried by the flower's pistil. However, it was found that some of the transgenic plants produced no seeds at all when pollinated with S3 pollen. This is a first direct evidence that by genetic manipulation one can introduce self-incompatibility.

The transgenic plants that failed to produce any seeds at all had normal levels of S3 protein for a plant containing an S3 gene, which enabled them to acquire the ability to completely reject S3 pollen. Some transgenic plants that produced a few seeds when pollinated with S3 pollen had levels of S3 protein that were much lower than normal, and those transgenic plants producing the most seeds did not have any detectable amount of S3 protein. This experiment shows that S-protein levels alone control a plant's ability to reject its own pollen—or pollen whose S allele type is identical to one of those contained in the flower's pistil.

OBJECTS OF THE INVENTION

It is an object of this invention to present a method for altering the self-incompatibility in flowering plants.

Another object of this invention is to provide a method for controlling the activity of the S locus involved in the self-pollination of plants.

These and other objects and advantages of this invention over prior art and a better understanding of its use will become readily apparent from the following description and are particularly delineated in the appended claims.

DESCRIPTION OF THE DRAWINGS

FIGS. 1a and 1b.

FIGS. 2a and 2b.

FIGS. 3a and 3b.

FIGS. 4a and 4b.

DETAILED DESCRIPTION OF THE INVENTION

The present invention describes the evidence of correlation between self-compatibility and S-genes in petunia plants. During the course of detailed studies involving the investigation of plant self-incompatibility, the involvement of proteins encoded by S-genes was demonstrated. The support for this new finding and ways of using it commercially are described herein.

A detailed embodiment of the present invention involving petunia plants is herein disclosed. However it is understood that the preferred embodiment is merely illustrative of the invention which may be embodied in various forms and applications. Accordingly, specific structural and functional details disclosed herein are not to be interpreted as limiting, but merely as a support for the invention as claimed and as appropriate representation for the teaching one skilled in the an to variously employ the present invention in any appropriate embodiment.

Figure 1A:
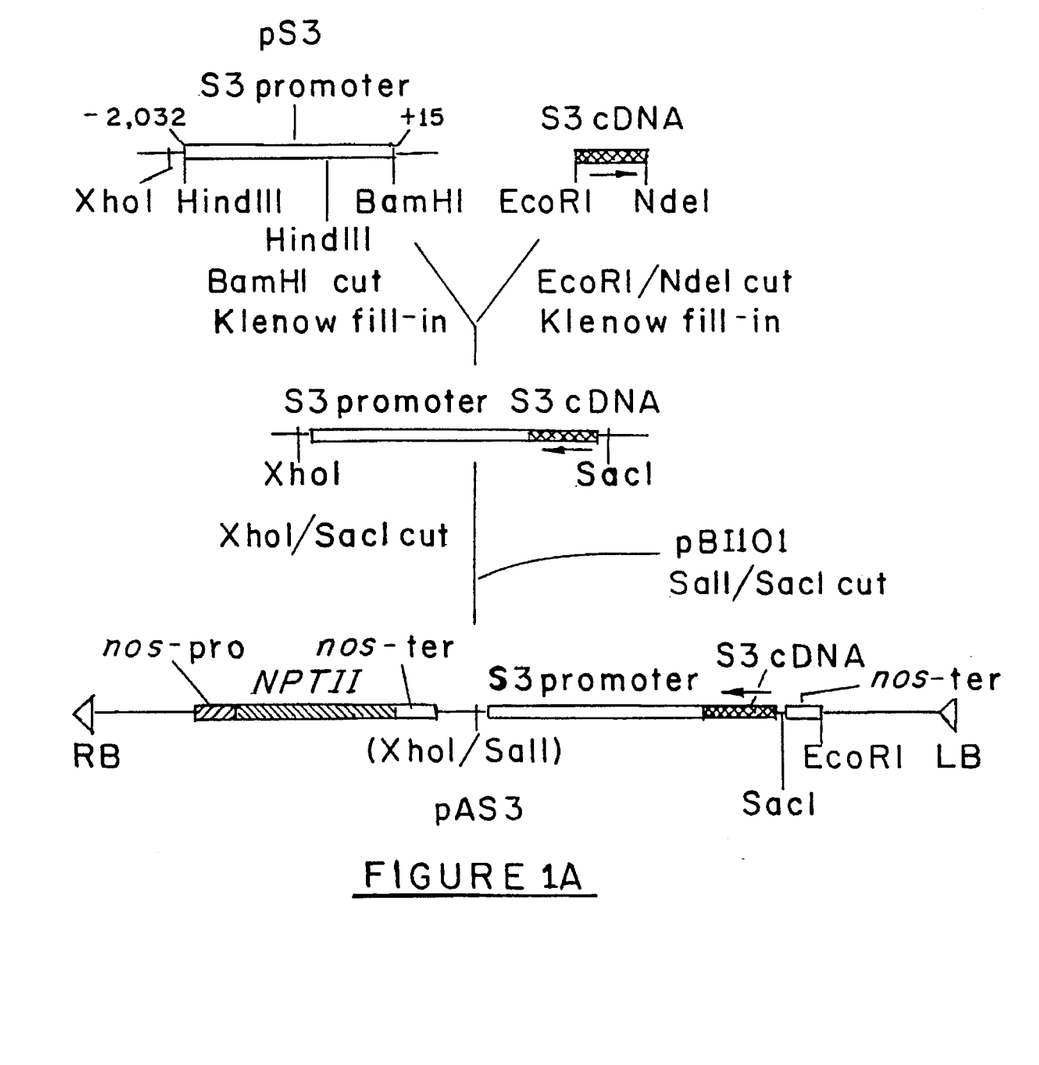
FIG. 1a presents a diagram of Antisense construct.

The applicant used both loss-of-function and gain-of-function approaches to ascertain whether the *P. inflata* S-proteins previously identified[9] do indeed control self-incompatibility interactions between pollen and pistil. In the former approach, he introduced antisense $S_3$-cDNA under the control of the promoter of the $S_3$-gene into *P. inflata* plants of $S_2S_3$ genotype by Agrobacterium-mediated transformation (FIG. 1a). This allowed him to determine whether inhibition of $S_3$-protein synthesis in the pistil abolished the ability of the transgenic plants to reject $S_3$-pollen.

Figure 1B:
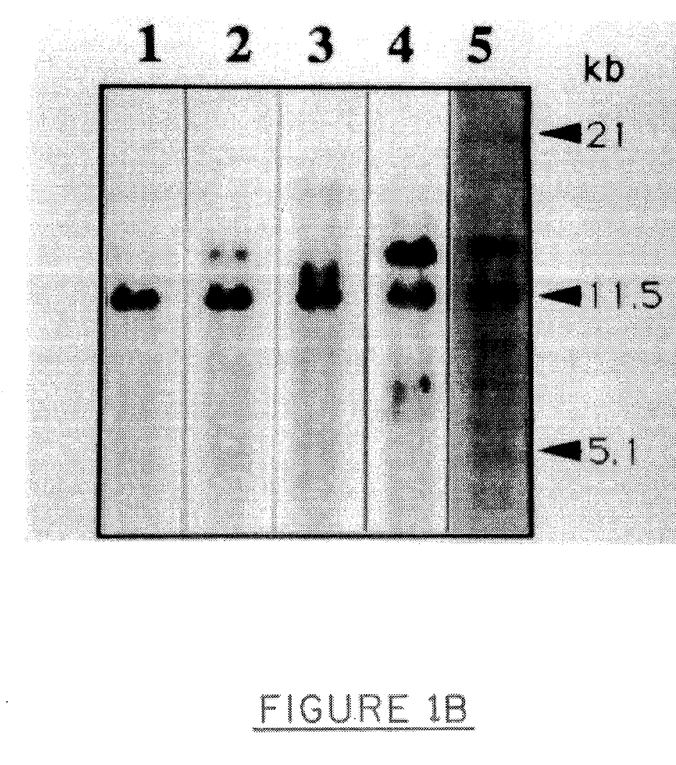
FIG. 1b presents a genomic Southern blot. Lane 1: parental $S_2S_3$ plant; lane 2: AS-37; lane 3: AS-4; lane 4: AS-14, lane 5: AS-27.

Forty-seven independent transgenic plants were self-pollinated to determine whether their self-incompatibility behavior had been affected. Thirty plants were found to set variable numbers of seeds, and 6 of them consistently produced a number of seeds comparable to that obtained from compatible pollination of *P. inflata* plants (approximately 200 per fruit). These 6 transgenic plants (AS-4, AS-14, AS-23, AS-27, AS-35, and AS-37) were chosen for further analysis. Genomic blot analysis of 4 of the plants revealed that, in addition to the 11.5 kb DNA fragment corresponding to the endogenous $S_3$-gene, they contained one to three insertions of the transgene (FIG. 1b).

To determine whether the breakdown of self-incompatibility in the 6 self-compatible transgenic plants resulted from loss of their ability to reject $S_3$-pollen, these plants were pollinated with pollen from $S_2S_3$ and $S_2S_2$ tester plants. AS-14, AS-23, and AS-37 rejected pollen from $S_2S_2$ plants, but accepted pollen from $S_2S_3$ plants, indicating that $S_3$-allele had been rendered nonfunctional, but $S_2$-allele was not affected. AS-4, AS-27, and AS-35 accepted pollen from both $S_2S_2$ and $S_2S_3$ plants, indicating that, in addition to $S_3$-allele, $S_2$-allele had also been rendered nonfunctional. AS-39, a self-incompatible transgenic plant, rejected pollen from both $S_2S_2$ and $S_2S_3$ plants.

Figure 2A:
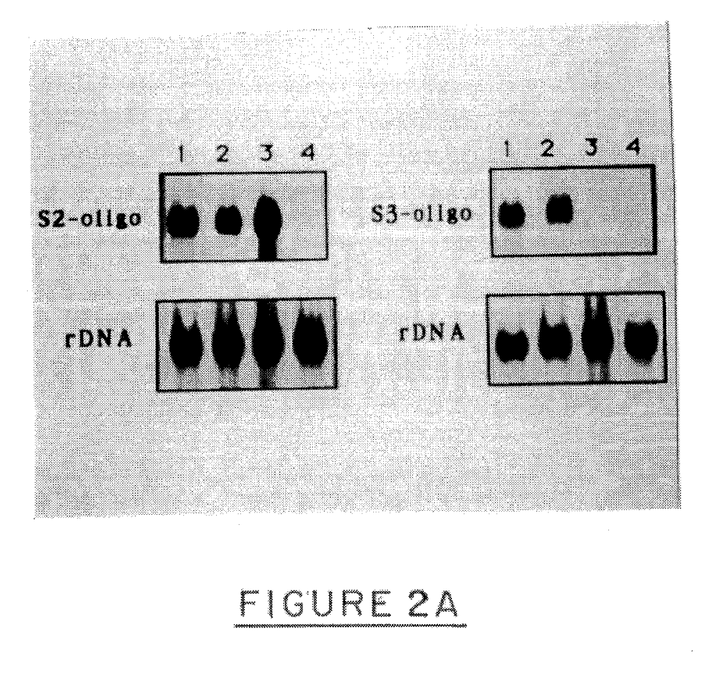
FIG. 2a presents Northern blots. Two identical RNA blots each containing total pistil RNA (10 μg per lane) of a parental $S_2S_3$ plant (lane 1), AS-39 (lane 2), AS-14 (lane 3), and AS-27 (lane 4).

Next the Applicant investigated whether the inability of the 6 self-compatible transgenic plants to reject $S_2$- or $S_3$-pollen was caused by inhibition of $S_2$- or $S_3$-protein synthesis. As shown in FIG. 2a, AS-14, which rejected $S_2$-allele but failed to reject $S_3$-allele, contained a normal level of $S_2$-RNA, but a nondetectable level of $S_3$-RNA; AS-27, which failed to reject either $S_2$- or $S_3$-allele, contained nondetectable levels of $S_2$-RNA and $S_3$-RNA; AS-39, which rejected both $S_2$- and $S_3$-alleles, contained normal levels of $S_2$- and $S_3$-RNA.

Figure 2B:
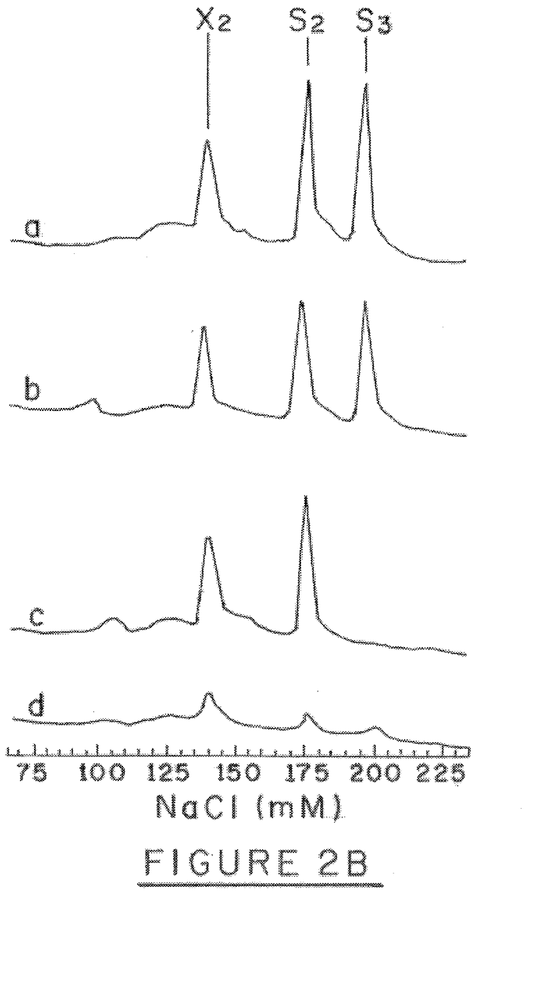
FIG. 2b presents FPLC profile.

The applicant then determined the amounts of $S_2$- and $S_3$-proteins in the pistils of the 6 self-compatible and 7 self-incompatible transgenic plants, and 7 parental $S_2S_3$ plants (FIG. 2b). Profile a in FIG. 2b is representative of these parental $S_2S_3$ plants. AS-14, AS-23, and AS-37 all contained normal amounts of $S_2$-protein, but drastically reduced amounts of $S_3$-protein (profile c in FIG. 2b shows AS-14). The amounts of both $S_2$- and $S_3$-proteins were drastically reduced in AS-4, AS-27, and AS-35 (profile d shows AS-27). In fact, the amounts of $S_3$-protein in the former 3 plants, and the amounts of $S_2$- and $S_3$-proteins in the latter 3 plants were lower than those present in immature buds which are fully receptive to serf pollen[9]. The amounts of $S_2$- and $S_3$-proteins of the 7 self-incompatible transgenic plants were comparable to those of the parental $S_2S_3$ plants (profile b shows AS-39).

The effect of the antisense $S_3$-gene was inheritable, because self-compatible plants were found in selfed progeny of AS-14 and AS-27. As in the parental transgenic plants, the amounts of $S_2$- and $S_3$-proteins also correlated perfectly with breeding behavior (results not shown). Thus, it was concluded from the antisense experiments that S-proteins are necessary for the pistil to reject self pollen.

The applicant used the gain-of-function approach to ascertain whether S-proteins alone are sufficient for the pistil to reject serf pollen. A 3.6 kb DNA fragment (FIG. 3a) containing the gene for $S_3$-protein[9, 18] was introduced into *P. inflata* plants of $S_1S_2$ genotype, and it was determined whether expression of the $S_3$-gene could confer on the transgenic plants a new $S_3$-allele specificity. Eighty-one transgenic plants were pollinated with pollen from $S_3S_3$ plants, and 4 plants, GS3-13, GS3-16, GS3-41, and GS3-55, were found to completely reject $S_3$-pollen. The rest set fruits of variable sizes with seed numbers ranging from 20 to 200, indicating that they were either partially or fully compatible with $S_3$-pollen.

The 4 transgenic plants that completely rejected $S_3$-pollen also rejected pollen from $S_1S_2$ plants. However, they set large fruits when selfed at the immature-bud stage when self-incompatibility is not yet expressed. Thus, the failure of the 4 plants to set fruits when pollinated with $S_1$-, $S_2$- and $S_3$-pollen was a true self-incompatible response, and not due to female sterility resulting from tissue culture manipulations.

Figure 3A:
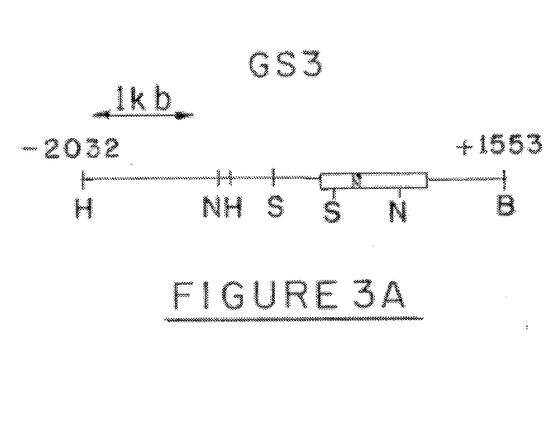
FIG. 3a presents a schematic representation of the genomic DNA used in transformation experiments.
Figure 3B:
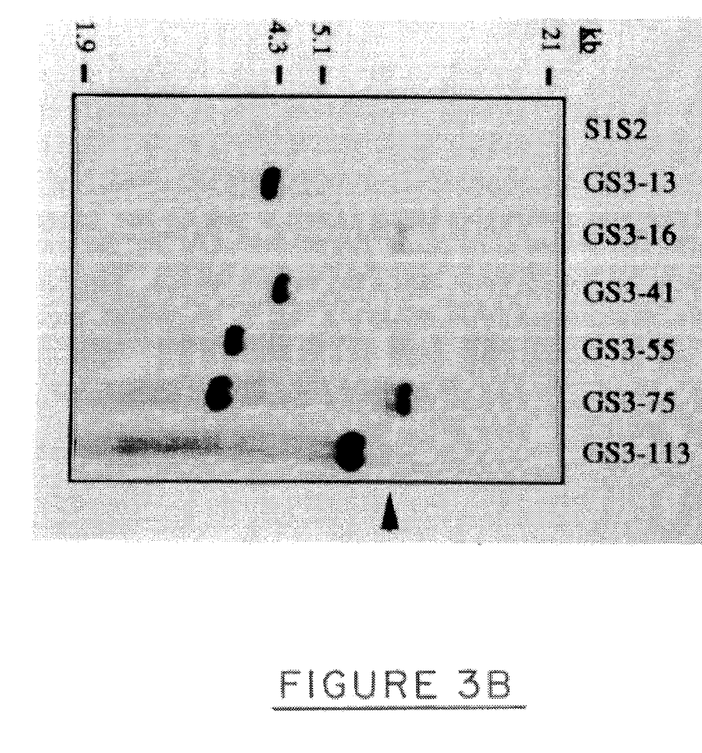
FIG. 3b presents a genomic Southern blot.

Genomic blot analysis revealed that all 4 plants contained a single insert of the transgene (FIG. 3b). Two other transgenic plants were also included in the analysis: GS3-75, a plant partially compatible with $S_3$-pollen (producing approximately 50 seeds per fruit, and GS3-113, a plant fully compatible with $S_3$-pollen (producing approximately 200 seeds per fruit). GS3-75 contained two inserts and GS3-113 contained one insert (FIG. 3b).

Figure 4A:
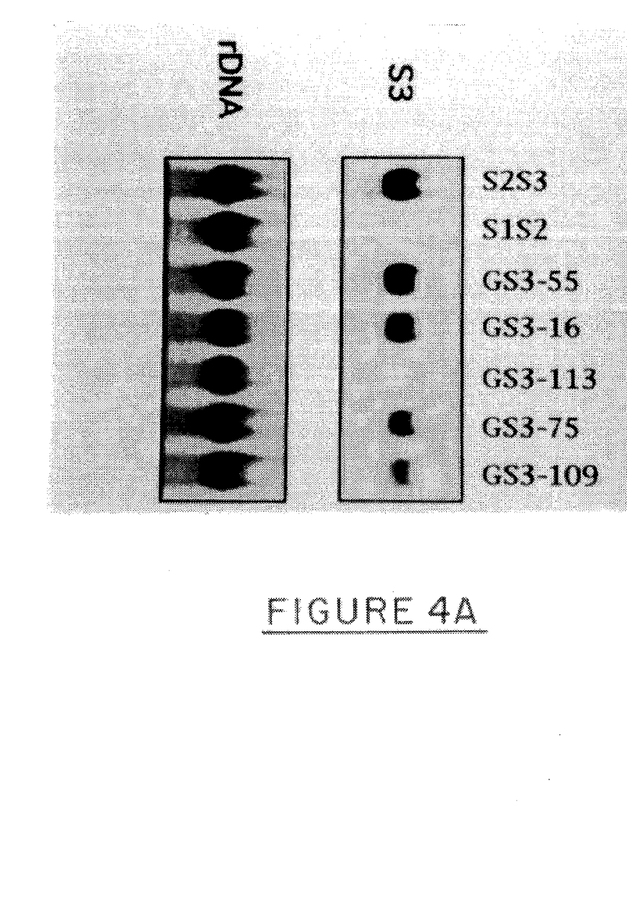
FIG. 4a presents a Northern blot.

To investigate whether the new $S_3$-allele specificity acquired by the 4 transgenic plants resulted from expression of the $S_3$-transgene in the pistil, the applicant first examined the level of $S_3$-RNA in the pistils of representative transgenic plants. As shown in FIG. 4a, GS3-16 and GS3-55, which completely rejected $S_3$-pollen, contained a normal level of $S_3$-RNA; GS3-75 and GS3-109, which were partially compatible with $S_3$-pollen, contained approximately 30% the normal level of $S_3$-RNA; GS3-113, which was fully compatible with $S_3$-pollen, did not contain any detectable $S_3$-RNA.

Figure 4B:
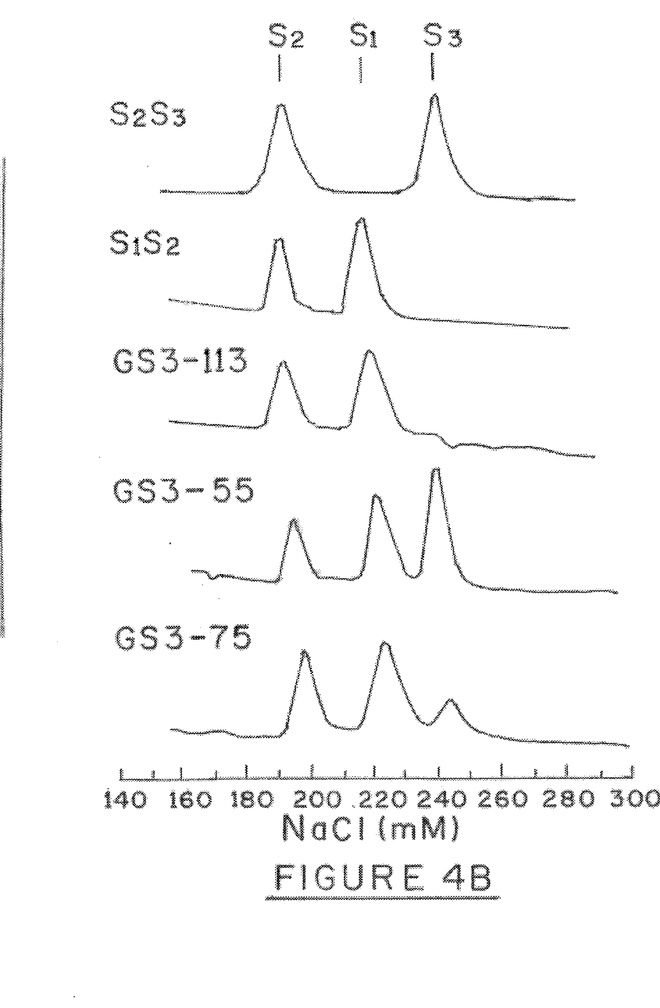
FIG. 4b presents FPLC profiles of the proteins.

The Applicant examined the mounts of $S_3$-protein in the pistils of 31 transgenic plants which included all the ones described above (FIG. 4b). All 4 plants that completely rejected $S_3$-pollen were found to produce a normal level of $S_3$-protein, in addition to producing normal levels of $S_1$- and $S_2$-proteins (compare the profile of GS3-55 with those of $S_1S_2$ and $S_2S_3$ plants). All 17 plants that were partially compatible with $S_3$-pollen produced the amounts of $S_3$-protein that were invariably much lower than normal (compare the profile of GS3-75 with that of GS3-55), and were comparable to or less than those present in immature buds of nontransgenic plants. All 10 plants that were fully compatible with $S_3$-pollen did not produce any detectable amount of $S_3$-protein (see the profile of GS3-113). Thus, it was concluded that the production of a normal level of $S_3$-protein in the pistil of the 4 transgenic plants conferred on them the ability to completely reject $S_3$-pollen. The finding that low level expression of the $S_3$-transgene in the pistil of mature flowers was not sufficient for rejection of $S_3$-pollen is similar to the previous findings that a low level of S-gene expression in immature buds of Petunia plants correlated with their inability to reject self pollen[9, 19].

Both the $S_3$-transgene and the antisense $S_3$-gene did not affect the self-incompatibility behavior of the pollen of the transgenic plants (data not shown). These results are consistent with the model of the S-locus proposed by Lewis which states that separate but closely linked genes control the self-incompatibility phenotype of the pollen and pistil[20].

In conclusion, the results presented in this invention provide direct in vivo evidence that the S-proteins of *P. inflata* are necessary and sufficient for the pistil to reject self pollen. This study also demonstrates the feasibility of using the antisense RNA approach to break down self-incompatibility. Furthermore, demonstration that the S-phenotype of a self-incompatible plant can be altered by the introduction of a single gene, the S-gene, should allow future dissection of the functional domains of the S-protein through mutagenesis studies.

EXAMPLE 1

Transformation of *P. inflata* Plants with Antisense $S_3$-gene, and Analysis of Transgenic Plants for Presence of the Transgene Antisense Construct The construct is presented in FIG. 1a. The promoter used to express the antisense $S_3$-cDNA was contained in a DNA fragment spanning from position −2,032 bp to position +15 bp of $S_3$-gene[18]. This DNA fragment had already been shown to confer pistil expression of the gene encoding b-glucuronidase (GUS) in transgenic *P. inflata* plants (unpublished results). The EcoRI-NdeI fragment of the $S_3$-cDNA used in the construct contained approximately 70% of the full-length $S_3$-cDNA previously reported[9]. Sense $S_3$-cDNA is indicated by an arrow pointing to the right; antisense $S_3$-cDNA is indicated by an arrow pointing to the left. The transcriptional termination signal was provided by the nopaline synthase terminator (nos-ter) present on a binary Ti-plasmid pBI101 (Clontech). The NPTII gene, which encodes neomycin phosphotransferase and confers kanamycin resistance in transgenic plants, is expressed by the promoter of the nos gene (nos-pro). The 2,047 bp $S_3$-promoter fragment was cloned into the HindIII and SmaI sites of pBluescript KS+ (Stratagene) to yield pS3. pS3 was digested with BamHI, and Klenow enzyme was used to create blunt ends. In the same fashion, blunt ends were created on an EcoRI-NdeI fragment of the $S_3$-cDNA, and this fragment was ligated in antisense orientation to the $S_3$-promoter in pS3. The $S_3$-promoter-$S_3$-cDNA fusion product was released by double digestion with XhoI and SacI, and the fragment was ligated into the SalI and SacI sites of pBI101. (The GUS gene present on pBI101 was removed during this step.)

Insertion of the Plasmid into a Plant

The recombinant Ti-plasmid, designated pAS3, was electroporated into *Agrobacterium tumefaciens* strain LBA4404. Leaf discs of *P. inflata* with $S_2S_3$ genotype were infected with the Agrobacterium by the co-cultivation method[21] on MS medium supplemented with benzylaminopurine (1.0 mg/L) and naphthalene acetic acid (75 mg/L). Shoots were regenerated on fresh MS medium[22] supplemented with kanamycin (100 mg/ml) and carbenicillin (500 mg/ml). Regenerated shoots were transferred to hormone-free MS medium containing the same concentrations of antibiotics to induce root formation.

Detection of the Protein Level in the Transgenic Plants

The level of protein present in the transgenic plants is represented in FIG. 1b, which is a radiograph of a filter from a genomic Southern blot. The filter containing EcoRI digests of genomic DNA was hybridized to a probe containing the full-length $S_3$-cDNA[9]. Genomic DNA was isolated from 2 g of frozen leaves with an Elu-Quick kit (Schleicher & Schell) following the manufacturer's protocol. Genomic DNA (5 mg) was digested with EcoRI, separated on a 0.8% agarose gel, and transferred to a Biotrans (+) nylon membrane (ICN). The membrane was prehybridized in a solution containing 5×SSC, 5×Denhardt's, 0.1% SDS, and 100 mg/ml of sheared and denatured fish sperm DNA for 2 hours at 65° C. Hybridization was carried out in the same solution with the addition of $^{32}$P-labelled S$_3$-cDNA for 16 hours at 65° C. The membrane was washed in 0.1×SSC and 0.1% SDS at 65° C. for 1 hour and exposed on X-ray film with an intensifying screen for 2 days at −70° C.

EXAMPLE 2

Analysis of the Amounts of S$_2$- and S$_3$-RNA, and S$_2$- and S$_3$-Proteins in a Parental S$_2$S$_3$ Plant and Transgenic Plants Analysis of the Amounts of RNA The analysis of the amount of the RNA was performed using Northern blots. The results are presented in FIG. 2a. Two identical RNA blots each containing total pistil RNA (10 µg per lane) of a parental S$_2$S$_3$ plant, AS-39, AS-14, and AS-27, were hybridized with two radiolabelled probes separately: S$_2$-oligo, an oligonucleotide specific to sense S$_2$-RNA, and S$_3$-oligo, an oligonucleotide specific to sense S$_3$-RNA. After autoradiography, the bound radiolabelled probes were removed from the blots, and the blots were hybridized with the third probe, rDNA, which encodes 25S rRNA of *P. inflata*. That step was performed in order to eliminate a possibility that a lack of signal is due to RNA degradation. Total RNA was isolated from pistils as previously described[10]. RNA samples were electrophoresed on 1.2% agarose/formaldehyde gels and transferred to Biotrans (+) membranes. The probe specific to sense S$_2$-RNA was a 51-mer with sequence: 5'-CAGAACATTGATTATAT-TATCTTCTTTTFFAAAACGCGAATACT-TGTCGCCAGT-3' (SEQ. ID NO:1). This sequence is complementary to a segment of S$_2$-cDNA encoding amino acid residues 48 to 64 of S$_2$-protein[9], which is located in the hypervariable region HVa of S-proteins[25]. The probe specific to sense S$_3$-RNA was a 54-mer with sequence: 5'-CAAATCATTGACAATTCTATCTTT-TAAGCTGAACGACACAAACTTATCTCCATC-3' (SEQ. ID NO:2). This sequence is complementary to a segment of S$_3$-cDNA encoding amino acid residues 48 to 65 of S$_3$-protein[9], which is also located in the HVa region. The two oligonucleotides were $^{32}$P-labelled at their 5' ends with T4 polynucleotide kinase. For hybridization with S$_2$- or S$_3$-oligo, the membranes were prehybridized as described in FIG. 1b, except at 45° C. for 2 hr, and hybridized in the prehybridization solution containing S$_2$- or S$_3$-oligo probe at 45° C. overnight. The membranes were twice washed in 0.1×SSC, 0.1% SDS at room temperature for 10 min each, and then washed with the same solution at 40° C. for 5 min. Autoradiography was carded out at −70° C. for 16 hr with an intensifying screen. The bound radiolabelled probes were removed from the membranes by boiling in 0.1×SSC and 0.1% SDS. For hybridization with the rDNA probe, the membranes were prehybridized as described for FIG. 1b in Example 1, and hybridized with the prehybridization solution containing $^{32}$P-labelled rDNA probe at 65° C. overnight. The membranes were washed in 0.1×SSC, 0.1% SDS at 65° C. for 1 hr, and autoradiographed at −70° C. for 1 hr with an intensifying screen.

Analysis of the Amounts of S$_2$- and S$_3$-Proteins

The protein level was measured using FPLC profiles. The results are presented on FIG. 2b. S$_2$- and S$_3$-proteins cannot be separated by SDS-PAGE due to their similar molecular weight[9], but can be separated from each other and from other pistil proteins by cation-exchange chromatography on a Mono-S column using the FPLC system (Pharmacia)[14]. The majority of pistil proteins flowed through during loading and washing of the column with 50 mM sodium phosphate (pH 6.0). The bound proteins that were eluted with the salt gradient consisted mainly of S-proteins and a pistil-specific ribonuclease, X2[14, 23]. The observed concomitant reduction of the level of S$_2$-protein in AS-27 (as well as in AS-4 and AS-35, not shown) and of the level of X2 in AS-27 by the antisense S$_3$-gene may be due to the sequence similarity between the 585 bp fragment of S$_3$-cDNA used in the antisense construct and the corresponding regions in the genes for S$_2$-protein[9] and RNase X2[23]. It has been previously observed that antisense RNA can inhibit the mRNA production from a target gene, as well as from genes with sequence similarity to the target gene[24].

Pistils were collected from freshly opened flowers of each plant and stored at −70° C. until use. Forty milligrams of pistils from each plant were ground to a fine powder in liquid nitrogen, with further grinding after the addition of 1 ml of the extraction buffer containing 50 mM Tris-HCl, pH 8.5, 10 mM EDTA, 1 mM PMSF, 1 mM CaCl$_2$, and 1 mM DTT. The crude extract was centrifuged at 12,000 g for 10 min, and the supernatant filtered through a 0.45 mm Millex-GV filter (Millipore) to remove unsedimented fine particles. The filtrate was applied to a Mono-S column (HR 5/5) which had been equilibrated with 50 mM sodium phosphate (pH 6.0). The bound proteins were eluted with a linear gradient of 0 to 500 mM NaCl in the same buffer at a flow rate of 0.5 ml/min. Proteins were monitored at $A_{280\ nm}$ with the sensitivity of the detector set to 0.1 AUFS. No discernible differences in the FPLC profiles for each plant were detected when two separate pistil extractions were used. The profile shown for each plant is one of the two runs.

EXAMPLE 3

Transformation of *P. inflata* Plants with S$_3$-gene, and Analysis of Transgenic Plants for Presence of the Transgene Transformation of *P. inflata* Plants with S$_3$-gene Schematic representation of the genomic DNA used in transformation experiments is presented in FIG. 3a. The DNA fragment, GS3, spans from position −2,032 bp to position +1,553 bp of the S$_3$-gene[18]. Open boxes denote the exons; the hatched box denotes the intron. Restriction enzyme sites are indicated with one-letter abbreviations: H, HindIII; N, Nde I; S, Stu I; B, Bsu 96I. The 3.6 kb genomic DNA (GS3) was released from the cloning vector pBluescript KS+ (Stratagene) by digestion with Xho I and Sac I, and the fragment was ligated into Sal I and Sac I sites of a binary Ti-plasmid vector pBI101. The GUS gene present on pBI101 was removed during this step. The recombinant Ti-plasmid was introduced into *P. inflata* plants by Agrobacterium-mediated transformation as described in FIG. 1b.

Analysis of Transgenic Plants for Presence of the Transgene

The analysis was performed using the genomic Southern blot technique. The falter containing HindIII digests of genomic DNA was hybridized with a radiolabelled probe of the full-length $S_3$-cDNA[9]. The genomic DNA was isolated from 1 nontransgenic plant $S_1S_2$ and 6 transgenic plants, as indicated above the blot. The results are presented on FIG. 3b. The arrow marks a weakly hybridizing DNA fragment of 9.9 kb which corresponds to the endogenous $S_2$-gene. The endogenous $S_1$-gene did not cross-hybridize with the $S_3$-cDNA probe under the conditions used. The DNA size markers are indicated. Two fragments seen in GS3-75 each resulted from one cut by HindIII within the integrated $S_3$-gene and a second cut in the genome. Genomic DNA was isolated from 2 g of frozen leaves as described in Example 1 for FIG. 1b. Genomic DNA (5 mg) was digested with HindIII, separated on a 0.8% agarose gel, and transferred to a Biotrans (+) nylon membrane (ICN). Prehybridization, hybridization, and washing of the falter were carded out as described in Example 1 for FIG. 1b. The filter was exposed on X-ray film at −70° C. for 48 h with an intensifying screen.

EXAMPLE 4

Analysis of the Amounts of $S_3$-RNA and $S_3$-Protein

Analysis of the Amounts of $S_3$-RNA

The amount of the RNA was measured by Northern blot. The results are presented in FIG. 4a. Each lane of the RNA blot contains 10 µg of total pistil RNA. Of the 7 plants analyzed, $S_2S_3$ and $S_1S_2$ are nontransgenic plants and the other 5 are transgenic plants. The blot was first hybridized with a radiolabelled oligonucleotide probe (S3) specific to $S_3$-RNA. After autoradiography, the bound radiolabelled probe was removed, and the blot was hybridized with a second probe (rDNA) which encodes 25S rRNA of P. inflata. The absence of a hybridizing fragment in the $S_1S_2$ sample confirms the specificity of the S3 probe used. The procedures for isolation of total RNA and for Northern analysis were identical to those described in Example 2. The $S_3$-RNA specific probe and the rDNA probe used were described in Example 2. After washing, the amount of radioactivity associated with each hybridizing band was determined using a Betagen Betascope. The relative amount of $S_3$-RNA in each transgenic plant to that of $S_2S_3$ plant was calculated after correction for the differences in the total amount of rRNA. The filters were then exposed on X-ray films at −70° C. for 30 min (rDNA probe) and 5 h (S3 probe) with intensifying screens.

Analysis of the Amounts of $S_3$-protein

The FPLC was used to measure the mounts of proteins. The profiles are presented in FIG. 4b. Total pistil protein of each plant was separated by a Mono-S column. Only the S-protein fractions are shown. Extractions of total pistil protein and conditions for column chromatography were as described in Example 2, except for three modifications: 5 mg of the pistils from each plant were used for extractions; the gradient was 2 times shallower; proteins were monitored with the sensitivity of the detector set to 0.02 AUFS. In addition, a different Mono-S column with the same dimension was used. Some of these modifications may account for differences in the salt concentration at which the same S-protein was eluted in the profiles shown here and in those shown in Example 2.

Thus, while I have illustrated and described the preferred embodiment of my invention, it is to be understood that this invention is capable of variation and modification, and I, therefore, do not wish or intend to be limited to the precise terms set forth, but desire and intend to avail myself of such changes and alterations which may be made for adopting the invention of the present invention to various usages and conditions. Accordingly, such changes and alterations are properly intended to be within the full range of equivalents and, therefore, within the purview of the following claims. The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Thus is described my invention and the manner and processing of making and using it in such full, clear, concise, and exact terms so as to enable any person skilled in the art to which it pertains, or with which it is most nearly connected, to make and use the same.

References

1. Frankel, R. & Galun, E. in *Monographs on Theoretical and Applied Genetics* (eds Frankel, R., Gall, G. A. E. & Linskens, H. F.) (Springer, Berlin, 1977)
2. de Nettancourt, D. in *Monographs on Theoretical and Applied Genetics* (eds Frankel, R., Gall, G. A. E. & Linskens, H. F.) (Springer, Berlin, 1977)
3. Bredemeijer, G. M. M. & Blass, J. (1981) *Theor. Appl. Genet.* 59, 185–190 (1981)
4. Anderson, M. A. et at. *Nature* 321, 38–44 (1986)
5. Kamboj, R. K. & Jackson, J. F. *Theor. Appl. Genet.* 71, 815–819 (1986)
6. Mau, S.-L. et al. *Planta* 169, 184–191 (1986)
7. Broothaerts, W. J. et al. *Plant Mol. Biol.* 14, 93–102 (1989)
8. Kirch, H.-H., Uhrig, H., Lottspeich, F., Salamini, F. & Thompson, R. D. *Theor. Appl. Genet.* 78, 581–588 (1989)
9. Ai, Y. et at. *Sex. Plant Reprod.* 3, 130–138 (1990)
10. Kheyr-Pour, A. et al. *Sex. Plant Reprod.* 3, 88–97 (1990)
11. Xu, B., Grun, P., Kheyr-Pour, A. & Kao, T.-h. *Sex. Plant Reprod.* 3, 54–60 (1990)
12. Ai, Y., Kron, E. & Kao, T.-h. *Mol. Gen. Genet.* 230, 353–358 (1991)
13. McClure, B. A. et at. *Nature* 342, 955–957 (1989)
14. Singh, A., Ai, Y. & Kao, T.-h. *Plant Physiol.* 96, 61–68 (1991)
15. Broothaerts, W., Vanvinckenroye, P., Decock, B., Van Damme, J. & Vendrig, J.C. *Sex. Plant Reprod.* 4, 258–266 (1991)
16. Singh, A. & Kao, T.-h. in *Sexual Reproduction in Flowering Plants* (eds Russell, S. D. & Dumas, C.) 449–483 (Academic Press, San Diego, 1992)
17. Sims, T. L. *Critical Rev. Plant Sci.* 12:129–167 (1993)
18. Coleman, C. E. & Kao, T.-h. *Plant Mol. Biol.* 18, 725–737 (1992)
19. Clark, K. R., Okuley, J. J., Collins, P. D. & Sims, T. L. *Plant Cell* 2, 815–826 (1990)
20. Lewis, D. *Heredity* 3, 339–355 (1949)
21. Horsch, R. B. et al. *Science* 227, 1229–1231 (1985)
22. Linsmaier, E. M. & Skoog, F. *Physiol. Plant* 18, 100–127 (1965)

23. Lee, H.-S., Singh, A. & Kao, T.-h. *Plant Mol. Biol.* 20, 1131–1141 (1992)
24. Oeller, P. W., Min-Wong, L., Taylor, L. P., Pike, D. A. & Theologis, A. *Science* 254, 437–439 (1991)
25. Ioerger, T. R., Gohlke, J. R., Xu, B. & Kao, T.-h. *Sex. Plant Reprod.* 4, 81–87 (1991)

or gain-of-function, wherein achieving said loss-of-function or gain-of-function comprises introducing genetic material comprising an S-locus gene into said plant, wherein regulation for loss-of-function requires that said genetic material comprise an anti-sense message of an

---

---

What is claimed is:

1. A solanaceous plant transformed with a gametophytic S-gene-specific anti-sense polynucleotide or a gametophytic S-gene-specific polynucleotide, wherein (1) transformation with said gametophytic S-gene-specific anti-sense polynucleotide transforms a gametophytic self-incompatible plant into a gametophytic self-compatible plant and (2) transformation with said gametophytic S-gene-specific polynucleotide transforms a gametophytic self-compatible plant into a gametophytic self-incompatible plant, and wherein said gametophytic S-gene encodes ribonuclease.

2. The plant of claim 1, wherein said gametophytic ε-gene-specific anti-sense polynucleotide is a cDNA that is controlled by a gametophytic S-gene promoter.

3. The plant of claim 2, wherein said cDNA is introduced to said plant as a component of a plasmid.

4. The plant of claim 3, wherein said plasmid is pAS3.

5. The plant of claim 1, wherein said gametophytic S-gene-specific polynucleotide is introduced to said plant as genomic DNA included in a plasmid.

6. The plant of claim 5, wherein said genomic DNA comprises GS3 or a segment thereof.

7. A method for promoting gametophytic self-compatibility or self-incompatibility in a plant comprising regulation of gametophytic S-locus activity, wherein said regulation of said gametophytic S-locus activity causes loss-of-function allele of the gametophytic S-gene, said allele being responsible for the self-incompatibility, wherein said anti-sense message comprises a genetic sequence constructed using the sequence or a portion of the sequence of said allele of the gametophytic S-gene responsible for the incompatibility, said message having a sufficient length to inhibit syntheses of active protein encoded by said allele of the gametophytic S-gene.

8. The method of claim 7, wherein said message is constructed using a sequence or sequence complementary to the hypervariable segment of said alleles of the gametophytic S gene.

9. The method of claim 7, wherein said genetic material is a DNA construct comprising anti-sense message and a regulatory region that promote expression of said anti-sense message in said plant.

10. The method of claim 7, wherein said genetic material is a DNA construct comprising the nucleotide sequence of an allele of the gametophytic S-gene and a regulatory region that promotes expression of said nucleotide sequence in said plant.

11. The method of claim 9, wherein preparation of said DNA construct comprises the steps of:

(a) preparing a DNA segment that encodes the hypervariable region of the gametophytic S-gene;

(b) ligating said hypervariable segment in the anti-sense orientation to a promoter sequence to obtain a promoter-antisense fusion; and (c) inserting said ligated promoter antisense fusion into a vector.

12. The method of claim 10, wherein preparation of said DNA construct comprises the steps of:
   (a) preparing a DNA segment that encodes the gametophytic S-gene;
   (b) ligating said segment in the sense orientation to a promoter sequence to obtain a promoter-sense fusion; and
   (c) inserting said ligated promoter-sense fusion into a vector.

13. The method of claim 7, wherein said anti-sense message comprises SEQ ID NO:1 or SEQ ID NO:2.

14. The method of claim 10, wherein said genetic material comprises the complement to SEQ ID NO:1 or SEQ ID NO:2.

* * * * *